(12) United States Patent
Kumar et al.

(10) Patent No.: US 7,092,087 B2
(45) Date of Patent: Aug. 15, 2006

(54) LASER-INDUCED BREAKDOWN SPECTROSCOPY FOR SPECIMEN ANALYSIS

(75) Inventors: Akshaya Kumar, Starkville, MS (US); Fang Yu-Yueh, Starkville, MS (US); Shane C. Burgess, Starkville, MS (US); Jagdish P. Singh, Starkville, MS (US)

(73) Assignee: Mississippi State University, Mississippi State, MS (US)

( * ) Notice: Subject to any disclaimer, the term of this patent is extended or adjusted under 35 U.S.C. 154(b) by 338 days.

(21) Appl. No.: 10/662,347

(22) Filed: Sep. 16, 2003

(65) Prior Publication Data

US 2005/0200843 A1    Sep. 15, 2005

(51) Int. Cl.
G01J 3/30 (2006.01)
(52) U.S. Cl. .................................. 356/318; 250/461.2
(58) Field of Classification Search ................ 356/318; 250/461.2
See application file for complete search history.

(56) References Cited

U.S. PATENT DOCUMENTS

| | | | |
|---|---|---|---|
| 4,927,307 A | 5/1990 | Fitzgerald et al. | |
| 5,128,882 A | 7/1992 | Cooper et al. | |
| 5,686,611 A | 11/1997 | Kim et al. | |
| 5,751,416 A | 5/1998 | Singh et al. | |
| 5,847,825 A * | 12/1998 | Alexander | 356/318 |
| 6,174,754 B1 | 1/2001 | Lee et al. | |
| 6,762,835 B1 * | 7/2004 | Zhang et al. | 356/318 |

OTHER PUBLICATIONS

Samek et al. "Laser induced breakdown spectroscopy: a tool for real time, in vitro and in vivo identification for carious teeth", Dec. 19, 2001, BMC Oral Health, vol. 1.*

Palmer-Toy, D.E., et al., "Direct Acquisition of Matrix-assisted Laser Desorption/Ionization Time-of-Flight Mass Spectra from Laser Capture Microdissected Tissues", Clinical Chemistry, vol. 46, No. 9, pp. 1513-1516, 2000.

Chaurand, P., et al., "Assesing Protein Patterns in Disease Using Imaging Mass Spectrometry", Journal of Proteome, vol. 6, pp. 676-681, 2003.

Jemal, A., et al., "Cancer Statistics, 2003", CA Cancer J. Clin., vol. 53, pp. 5-26, 2003.

"Cancer Facts and Figures 2003", American Cancer Society, www.cancer.org, 2003.

Srinivas, P.R., et al., "Proteomics in Early Detection of Cancer", Clinical Chemistry, vol. 47, No. 10, pp. 1901-1911, 2001.

Ramanujam, N., et al, "Fast amd Noninvasive Fluorescence Imaging of Biological Tissues In Vivo Using a Flying-Spot Scanner", IEEE Trans. On Biomed. Engg., vol. 48, No. 9, pp. 1034-1041, 2001.

Ntziachristos, V., et al., "Fluorescence imaging with near-infrared light: new technological advances that enable in vivo molecular imaging", Eur. Radio., vol. 13, pp. 195-208, 203.

(Continued)

*Primary Examiner*—Hoa Q. Pham
*Assistant Examiner*—Kara Geisel
(74) *Attorney, Agent, or Firm*—DLA Piper Rudnick Gray Cary US LLP

(57) ABSTRACT

The present invention is directed to an apparatus, a system and a method for detecting the presence or absence of trace elements in a biological sample using Laser-Induced Breakdown Spectroscopy. The trace elements are used to develop a signature profile which is analyzed directly or compared with the known profile of a standard. In one aspect of the invention, the apparatus, system and method are used to detect malignant cancer cells in vivo.

33 Claims, 13 Drawing Sheets

Diagram of LIBS setup.

OTHER PUBLICATIONS

Peña L., et al., "Canine inflammatory mammary carcinoma: histopathology, immunohistochemistry and clinical implications of 21 cases", Breast Cancer Res. and Treat., vol. 78, pp. 141-148, 2003.

Schafer, K.A., et al., "A Canine Model of Familial Mammary Gland Neoplasia", Vet Pathol, vol. 35, pp. 168-177, 1998.

Vail, D.M., et al., "Spontaneously Occurring Tumors of Companion Animals as Models for Human Cancer", Cancer Investigation, vol. 18, No. 8, pp. 781-792, 2000.

E. Gregory MacEwen, "Spontaneous tumors in dogs and cats: Models for the study of cancer biology and treatment", Cancer Metastasis Rev., vol. 9, pp. 125-126, 1990.

Yueh, F.Y., et al., "Laser-induced Breakdown Spectroscopy, Elemental Analysis", Encyclopedia of Analytical Chemistry, John Wiley and Sons, Ltd., Chisheter, U.K., pp. 2066-2287, 2000.

Radziemski, L.J., et al., "Spectrochemical Analysis Using Laser Plasma Excitation", Laser-Induced Plasmas and Applications, Marcel Dekker, New York, NY, Chapter 7, pp. 295-325, 1989.

Thiem, T.L., et al., "Quantitative Simultaneous Elemental Determinations in Alloys Using Laser-Induced Breakdown Spectroscopy (LIBS) in an Ultra-High Vacuum", Applied Spectroscopy, vol. 48, No. 1, pp. 58-64, 1994.

Rusak, D.A., et al, "Fundamentals and Applications of Laser-Induced Breakdown Spectroscopy", Crit. Reviews in Anal. Chem., vol. 27, No. 4, pp. 257-290, 1997.

Rai, A.K., et al., "High temperature fiber optic laser-induced breakdown spectroscopy sensor for analysis of molten alloy constituents", Rev. Sci. Instrum., vol. 73, No. 10, pp. 3589-3999, 2002.

Samek, O., et al., "Application of laser-induced breakdown spectroscopy to in situ analysis of liquid samples", Opt. Eng., vol. 38, No. 8, pp. 2248-2262, 2000.

Kwiatek, W.M., et al., "Investigation of trace elements in cancer kidney tissues by SRIXE and PIXE", Nuclear Instruments and Methods in Physics Research B 109/110, pp. 284-288, 1996.

Ershaidat, N.M., et al., "Elemental Analysis of Colorectal Cancerous Samples using XRF Techniques", See enidal@yu.edu.jo, mamoods@yu.edu.jo, 2002.

Kumar, A., et al., "Characterization of Malignant Tissue Cells Using Laser-induced Breakdown Spectroscopy", Optics Express (under review), 2003.

Kumar, A., et al, "Laser Induced Breakdown Spectroscopy: Application to Life Sciences", Mississippi State University, Invention Disclosure No. 03-0414-50, 2003.

Ng, C.W., et al., "Detection of Sodium and Potassium in Single Human Red Blood Cells by 193-nm Laser Ablative Sampling: A Feasibility Demonstration", Analytical Chemistry, vol. 72, No. 1, pp. 247-250, 2000.

Xu, B.J., et al., "Direct Analysis of Laser Capture Microdissected Cells by MALDI Mass Spectrometry", American Society for Mass Spectrometry, vol. 13, 1292-1297, 2002.

* cited by examiner

LASER-INDUCED BREAKDOWN SPECTROSCOPY FOR SPECIMEN ANALYSIS

This invention was made with Government support under DE-FC26-98FT40395 awarded by the U.S. Department of Energy. The Government may have certain rights in the invention.

BACKGROUND OF THE INVENTION

1. Field of the Invention

The present invention, in one aspect, relates to the field of spectroscopy, and devices and methods through which it is applied. In a more particular aspect, the invention relates to spectroscopic devices and methods using Laser Induced Breakdown Spectroscopy (LIBS) in the detection of trace metal elements in the various parts of living organism. The invention also relates to the detection of normal and malignant tissue or cancer cells using LIBS devices and methods according to the invention. The invention also relates to a method and device that can provide real-time on site measurement of trace metals in a plant or animal. It can be used to detect cancer or trace element deficiency related to other health problems in either animals or plants.

2. Related Art

U.S. Pat. No. 4,927,307 to Cremers et al discloses an apparatus and method for using Laser-Induced Breakdown Spectroscopy (LIBS) to identify contaminants in liquid samples.

U.S. Pat. No. 5,847,825, to Alexander discloses an apparatus and method for using Laser-Induced Breakdown Spectroscopy (LIBS) to examine paints and coatings.

U.S. Pat. No. 5,128,882 to Cooper et al discloses a fiber optic cone penetrometer probe to irradiate soil with UV or visible light to generate a fluorescence, reflection, or absorption spectrum of soil contaminants. The fluorescence spectroscopy described in the patent generates information for classifying certain molecular species, but does not form a plasma and is generally insensitive to atomic species, which are important to the identification of metal contamination.

U.S. Pat. No. 5,751,416 to Singh et al discloses analytical methods involving Laser-Induced Breakdown Spectroscopy (LIBS). The disclosure is limited to utilizing LIBS methodology to examine inorganic specimens in environmental applications to determine the presence materials such radioactive elements or toxic metals in off-gas emissions.

U.S. Pat. No. 6,174,754 to Theriault et al discloses a cone penetrometer involving Laser-Induced Breakdown Spectroscopy (LIBS) for soil sample analysis.

All documents cited herein are incorporated by reference for all purposes.

3. Background

The optimum concentration and balance among various trace elements is vital for the health of both plants and animals. For example, an imbalance in certain trace elements such as sodium, potassium or others can indicate a number of health disorders. In animals such imbalances can cause or be indicative of a disorder to the nervous system or decreased functioning of the brain, liver, kidney or other vital organ. An imbalance in one or more trace elements can also affect or indicate a disorder in plants at various stages of growth, either at germination, blossoming, or at another stage of growth.

Recent surveys reveal that in 2003, breast cancer will be newly diagnosed in over 200,000 women in the United States.[1,2] Early diagnosis, especially before the cancer has metastasized to regional lymph nodes is essential. Breast lumps can be found by self-examining or a physical examination by a medical practitioner. Primary diagnosis is currently done using ultrasound and/or mammography tests. In the regular course of diagnosis, a breast biopsy is needed to determine whether a lump is malignant or benign. This requires that the lump, or some part thereof be first extracted by surgery and then analyzed using pathological methodology to determine whether the biopsy contains cancerous cells. Recently, imaging and molecular biology techniques have been developed for assisting with cancer diagnosis.[3-5]

Existing technologies for cancer detection include radiology NMR imaging and biopsy followed by histopathological examination. Newer methods, which are still experimental include matrix assisted laser desorptionlionization (MALDI) technique, and surface enhanced laser/desorption ionization (SELDI) technique. These different methodologies are very expensive and can also require significant time for analyzing a sample in a laboratory. Current methods for definitive identification of malignancy within a breast can be a difficult and painful process because a sample from a suspicious tissue mass must be extracted and then analyzed to determine whether it is malignant.

Laser Induced Breakdown Spectroscopy (LIBS) is a method for detecting the presence of various elements in a sample by directing a high power emission from a laser onto the sample to form a plasma. The plasma is then analyzed spectroscopically to determine the composition of the sample.

The LIBS methodology, through the discovery of this invention, now offers promise as a method suitable for incorporating with a probe to detect trace metal profiles in various biological media, because it is highly sensitive and requires no sample preparation. The LIBS method can include delivery of laser energy to a sample through air utilizing high power densities to ionize a sample. According to the invention, fiber optic cable can be used successfully to obtain LIBS spectral data from a remote location allowing analysis of a sample located at a considerable distance from the excitation laser and analyzing equipment. Further information about Laser Induced Breakdown Spectroscopy (LIBS) is found in U.S. Pat. No. 5,751,416 issued May 12, 1998, and in U.S. patent application Ser. No. 10/098,368, filed Mar. 18, 2002.

In the practicing the instant invention, LIBS surpasses the demanding and expensive methodology currently associated with cancer identification and produces results at a lower cost, in less time, providing spectral profiles that correlate to classifications of cancer while at the same time eliminating many of the complexities and risks inherent in tissue analysis by biopsy. According to the invention, LIBS has additional uses than known methods of analyzing biological samples including uses for tissue identification and forensic analysis of trace elements in a biological sample.

SUMMARY OF THE INVENTION

An object of the invention is a laser-induced breakdown spectroscopy (LIZBS) apparatus having a laser light source, a detector, and a probe for directing laser light from the laser light source to a sample in vivo; wherein the laser light is directable through the probe to a sample in vivo to generate an emission spectrum and said emission spectrum from said sample is capturable for a recording, a real-time analysis or a subsequent analysis. Another object is an apparatus further comprising a data acquisition or analysis system with optionally a separate data processor. Another object is such an apparatus in which the laser light is transmitted to the probe through a harmonic separator for directing laser light from the laser light source. Another object is such an apparatus further comprising a dichroic mirror for reflecting the laser light from the harmonic separator. Another object is such an apparatus further comprising a coupling lens for coupling the laser light at an input end of a multi-mode optical fiber. Another object is such an apparatus wherein the emission spectrum is collected either in the same fiber or in another fiber to travel in a backward direction to a spectrometer. Another object is such an apparatus wherein the laser light source is a $CO_2$ laser, a Ruby laser, a long-pulse YAG laser, an Alexandrite laser, an ER:YAG laser, an intense pulsed light laser, a KTP laser, a diode laser, a pulse dye laser or a pulsed Nd:YAG laser. Another object is such an apparatus wherein apparatus is part of a laser scalpel.

Still another object of the invention is a laser-induced breakdown spectroscopy (LIBS) system comprising a laser light source, a detector, and a biological sample, wherein the laser light is directable to the biological sample to generate an emission spectrum and said emission spectrum from said biological sample is capturable for a recording, a real-time analysis or a subsequent analysis.

Still yet another object of the invention is a method of using a laser-induced breakdown spectroscopy (LIBS) system, said method comprising directing laser light from a laser light source to a biological sample, generating an emission spectrum from the biological sample, detecting the emission spectrum, and capturing the emission spectrum for a recording, a real-time analysis or a subsequent analysis. Another object is such a method comprising comparing the emission spectrum with a control emission spectrum to determine the presence or absence of health of a host organism from which the biological sample is obtained. Another object is such a method and further comprising analyzing the emission spectrum to determine the presence or absence of at least one trace element. Another object is such a method comprising analyzing the emission spectrum to determine the quantity of at least one trace element. Another object is such a method comprising evaluating the light emitted from the sample by calculating the concentration of at least one chemical element from sample; comparing the concentration of the chemical element in the sample with a range of concentrations of the chemical element in a standard; and classifying the sample as normal or abnormal. Another object is such a method comprising directing the laser light through a probe onto the sample in vivo. Another object is such a method wherein the sample is selected from the group consisting of: blood, nail, hair, tissue or biological fluid. Another object is such a method wherein the sample source is a human, an animal or a plant, or a combination thereof. Another object is such a method wherein the method is practiced to detect cancer, or in one embodiment breast cancer. Another object is such a method wherein the method is practiced to detect or diagnose a disease or disorder. Another object is such a method wherein the method is practiced in a forensic analysis. Another object is such a method wherein the method is practiced utilizing a laser scalpel.

BRIEF DESCRIPTION OF THE INVENTION

The invention relates to Laser Induced Breakdown Spectroscopy (LIBS) to precisely distinguish between malignant cells and normal cells in real-time, either directly in vivo or in an extracted sample. The invention is also a method and device that can provide real-time on site measurement of trace metals in a plant or animal to detect trace element deficiency related health problems in plants or animals. The invention also is directed to forensic uses such identification of the source of a sample or in the detection of trace elements, such as those found in nail, hair, blood, etc., all using Laser Induced Breakdown Spectroscopy.

DESCRIPTION OF THE FIGURES

The foregoing summary, as well as the following detailed description, will be better understood when read in conjunction with the appended drawings. For the purpose of illustrating the invention, there is shown in the drawings embodiments which are presently preferred, it being understood that this invention is not limited to the precise arrangements and instrumentalities shown.

DETAILED DESCRIPTION OF THE INVENTION

Figure 1:
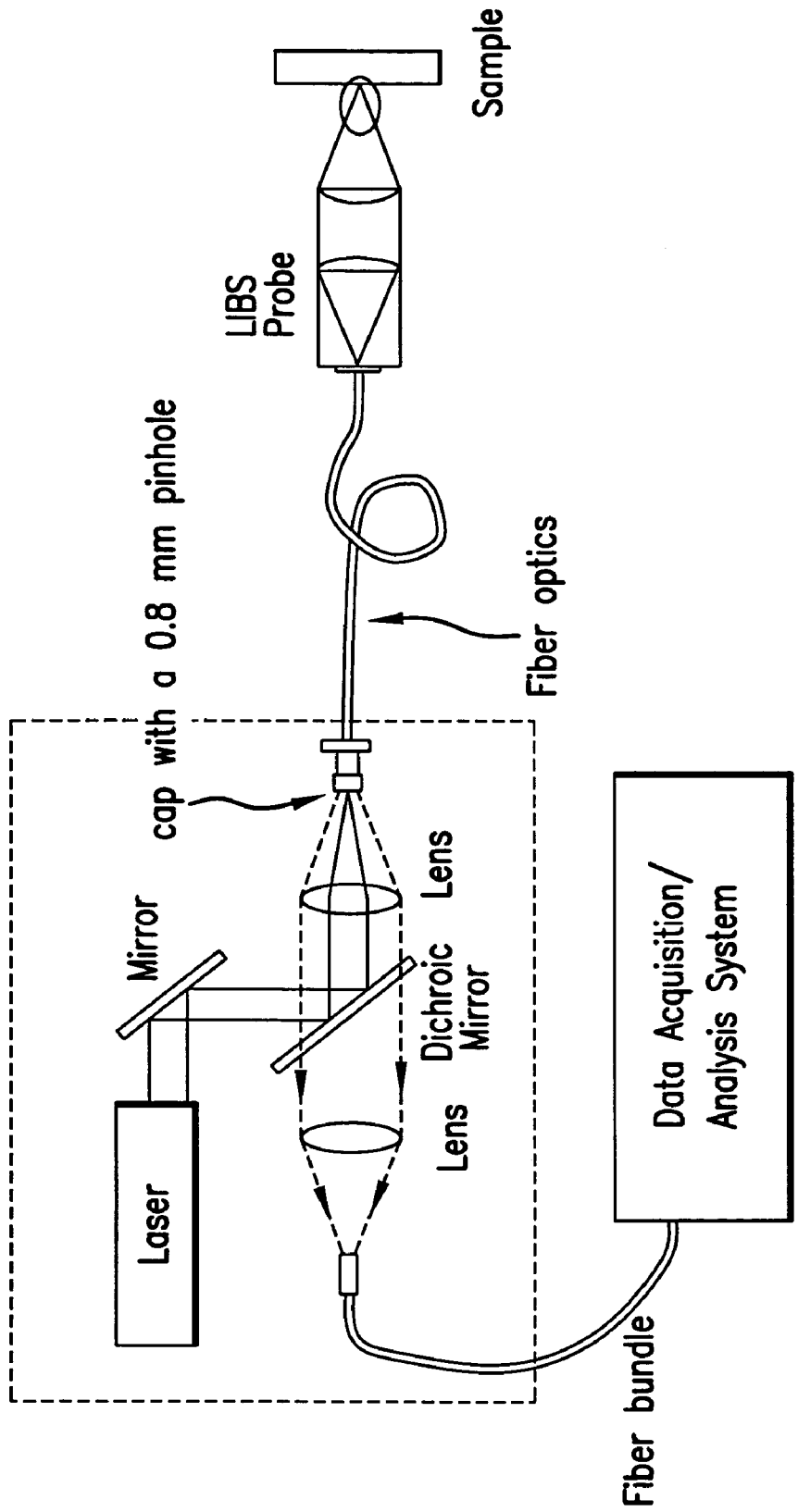
FIG. 1 is a conceptual design of an LIBS apparatus with a fiber optic cable in accordance with an embodiment of this invention.

While this invention is satisfied by embodiments in many different forms, there will herein be described in detail preferred embodiments of the invention, with the understanding that the present disclosure is to be considered as exemplary of the principles of the invention and is not intended to limit the invention to the embodiments illustrated and described. Numerous variations may be made by persons skilled in the art without departure from the spirit of the invention.

For purposes of this invention, the term "biological sample" refers to any specimen of, or excreted from, a living organism. The living organism may be a virus, a fungus, and any single cell organism or multicellular organism such as an animal or plant. Animals are all vertebrate or invertebrate creatures, including humans.

The invention is directed to a method and device that does not require the two step process of tissue extraction and analysis before it is determinable whether a tissue mass is malignant. In the method and device of the invention, the spectral data result can be collected and evaluated in real time from a sample in vivo. A major advantage of LIIBS device and method of the invention is that it can be practiced in real-time with either zero or minimal sample preparation.

Laser Induced Breakdown Spectroscopy (LIBS) can use an optical fiber to deliver a laser pulse to a biological sample such as blood, tissue, nail or hair. The high intensity laser light creates a spark or plasma in the sample and the emission from the spark is collected either in the same fiber or another fiber directed backward to the spectrometer. In LIBS each metal has its own set of emissions to form a fingerprint spectrum which can be used to identify an element.

The discrete spectral signature of different elements present in any sample can be monitored on a computer screen. The LIBS data from a trace element analysis of a sample can be used to correlate the health of host animal or plant. There are significant differences in the content of different metals such as calcium, aluminum, and iron between tissue samples that are either malignant or normal. These differences can be detected by the invention. In addition, the imbalance of trace elements such as sodium, iron, aluminum, potassium, calcium, and many others can indicate a number of concerns such as a nerve disorder or abnormal functioning of a vital organ.

The present invention provides a Laser Induced Breakdown Spectroscopy method and device for diverse life science analytical applications. According to one embodiment, a pulsed Nd:YAG laser light is delivered from a laser system using a fiber optic probe. The light can be focused on a specimen such as a drop of blood, tissue, nail or hair, etc, either in vivo or extracted. In another aspect of the invention, different laser sources can be used such as a $CO_2$ laser, a Ruby laser, a long-pulse YAG laser, an Alexandrite laser, an ER:YAG laser, an intense pulsed light laser, a KTP laser, a diode laser, or a pulse dye laser. These different lasers can be used for detecting the presence as well as the concentrations of elements.

The high temperature created by the laser beam on the specimen surface results in plasma formation, (i.e., the atomization of elements in the specimen.) The light emission from this plasma, otherwise known as a spark, can be collected by another or the same fiber and passed in the reverse direction to the spectrometer. The discrete spectral signature of different elements present in the sample can be monitored on a computer screen. Data from the trace element analysis can be used to assess the health of the subject organism.

The procedure makes use of an optical fiber probe that can be inserted into the sample tissue. A pulsed laser beam may then be used to generate a high temperature plasma at the probe tip which breaks down the exposed tissue and stimulates light emission that is transmitted back through the fiber to a photo-detector. An algorithm can then be applied to process the signal to classify the tissue qualitatively as for instance, being malignant or non-malignant.

Although much breast cancer research is currently focused on the fundamental molecular pathology of the various categories of breast cancer, a critical applied clinical issue is early, rapid and accurate diagnosis and complete surgical removal of breast cancer. The recent decrease in breast cancer mortality is linked to improvements in screening and early detection. Development of more sensitive and rapid screening techniques offer further advantages, especially for younger women whose breast density may preclude adequate screening by conventional mammography. Furthermore, surgical interventions that are less radical have a significant positive impact on patient's emotional and psychological well-being.

The interaction of high-power laser light with a target sample has been a topic of study in many fields of research and analysis.[6,7] The use of lasers to vaporize, dissociate, excite or ionize species on material surfaces has the potential of becoming a powerful analytical tool. When a high-power laser pulse is focused onto the target of any kind of material (solid, liquid, gas) the irradiation in the focal spot leads to rapid local heating, intense evaporation and degradation of the material. Because a sample of nanograms or micrograms is ablated in a time frame that is roughly in femoseconds to nanoseconds, depending on the laser pulse width, the whole process is considered as non-traumatic.

LIBS is suitable for rapid on-line elemental analysis of different phases of material and has proved its importance in obtaining analytical atomic emission spectra directly from solid, liquid, and gaseous samples.[8-11] LIBS has various advantages over conventional laboratory based chemical analysis techniques. It is a sensitive optical technique with high spatial resolution, in a small focal spot. In the process vaporization and excitation of the sample materials occurs directly in one step.

Previous researches have shown significant differences in concentrations of trace elements between normal and cancerous tissue cells.[12,13] LIBS, an elemental composition analysis technique, provides useful data to correlate elemental concentration and cancerous tissue cell. Information from the spectra of various cancerous and normal tissues allows the development of this invention for real-time diagnosis of breast cancer. For real-time diagnosis of breast cancer, a micro-size optical fiber probe (probe or micro-probe) using a 500μm optical fiber. A micro-lens is attached to the tip of the fiber and is used to directly send a pulsed laser beam or spark onto/into a potential breast tumor mass. The light emitted from the tissue mass is carried back to the spectrometer by the same set of optical fibers. The emitted atomic emission from the laser spark is dispersed by the spectrometer and the atomic signature identified. The diagnosis can be achieved in real-time, directly in the patient, optionally using a local anesthetic.

A primary advantage of the invention over other techniques is that it has real time, online measurement capability and is minimally traumatic. Other techniques like X-ray fluorescence and the mass spectroscopy all require biopsy followed by time consuming sample preparation and processing.

One aspect of the invention is to provide a method of rapid accurate diagnosis of breast cancer and for surgical intervention. Another aspect of the invention is the ability to use an optical fiber micro-probe to distinguish other cancerous tissue cells from normal tissue, in real-time directly in vivo. Another aspect of the invention is to provide a method for accurate diagnosis of bladder, colon, endometrial, lung, ovarian, prostate, or rectal cancer. Other types of cancer can also be detected by this invention.

The invention, according to another embodiment, uses an optical fiber bundle for delivering the pulsed laser power to produce a spark as well as for collecting the resulting emission from the spark for quantitative elemental analysis with greater accuracy and a lower detection limit.[10] The optical fiber bundle can, for instance, consist of a central fiber and a ring of surrounding fibers. Other configurations can be determined by those skilled in the art.

In another aspect of the invention, the micro-probe may be used as a surgical tool or "laser scalpel." When used as a laser scalpel, the same laser that is used to cut and cauterize tissues may be used to provide a diagnostic spectrum in real-time. Such diagnostic spectra may be analyzed directly by computer in real-time. Because there is no delay in assessment of surgical margins, neoplastic masses may be removed in their complete entirety with confidence, while at the same time sparing a maximum amount of healthy tissue.

In another aspect of this invention, computer software differentiates between cancer and normal tissue based on the intensity and ratio of different trace elements present in the tissue cell. The software uses the spectra of different tissues as the database for the fast data processing. Data processing techniques, such as Artificial Neural Network (ANN) or Principal Component Analysis (PCA) are used to evaluate information extracted from the spectral data. The software is based on the selected data processing techniques to process the collected data either in real-time or near real-time.

Figure 2:
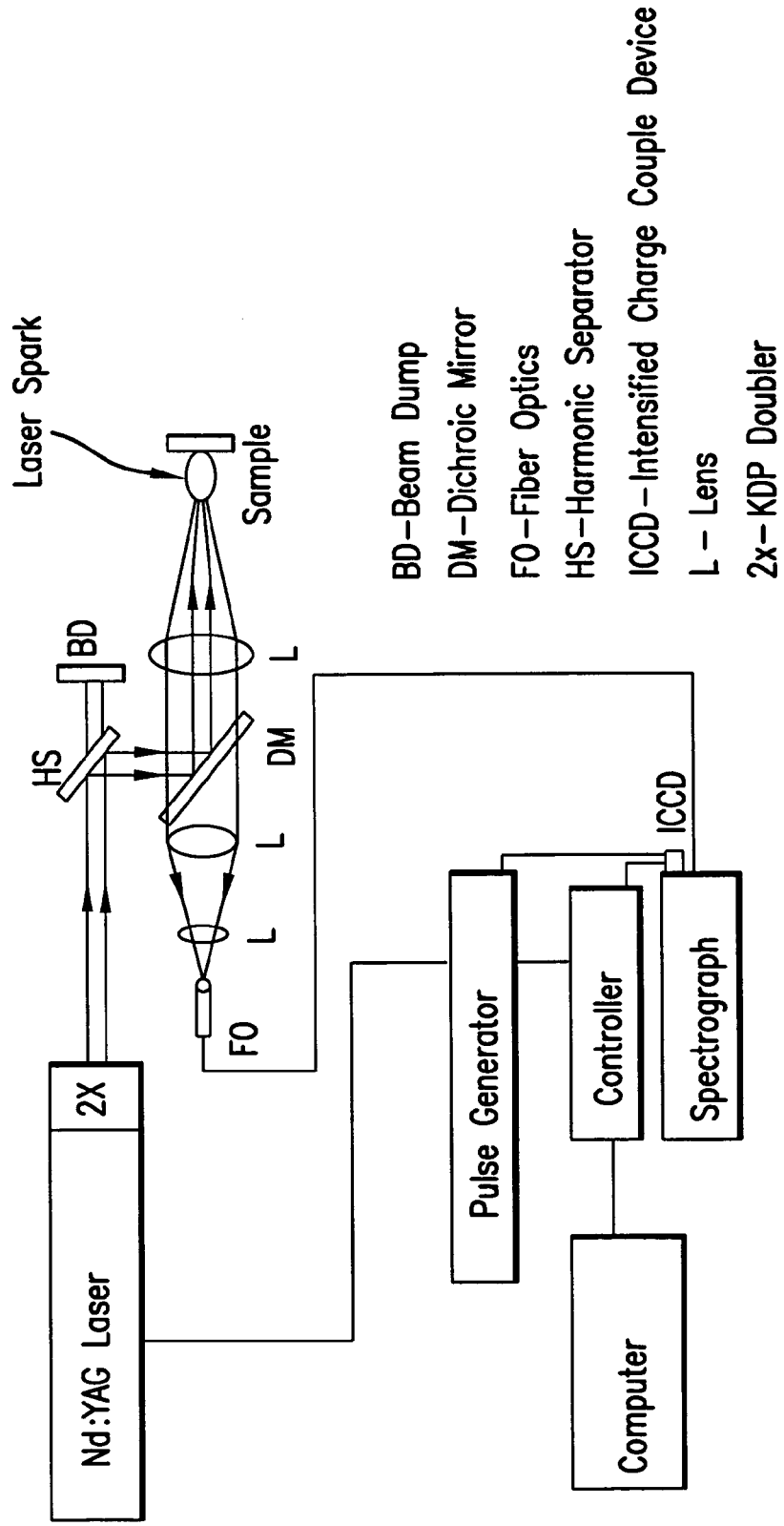
FIG. 2 is a conceptual design of an LIBS optical mechanism invention in accordance with an embodiment of this invention.

A broad schematic diagram of a micro-probe sensor setup is shown in FIG. 1 with a Data Acquisition/Analysis System, an LIBS System, a Probe and Sample. A more detailed schematic diagram of the LIBS optical mechanism is shown in FIG. 2 in which a pulsed laser from a Nd:YAG Laser system is directed into the optical fiber probe using two mirrors. The harmonic separator mirror reflects the laser beam into the dichroic mirror (DM) which reflects the beam through a lens to the probe cap and onto the specimen. The light emission from the laser-produced plasma on the specimen is collected by a set of lens and passed to the fiber optic bundle which transmits the LIBS signal to the detection system, a spectrograph. A gated intensified charge coupled device is used as the detector with its controller. Computer software can assist the operator to identify and/or quantify the elements present in the sample.

Figure 10A:
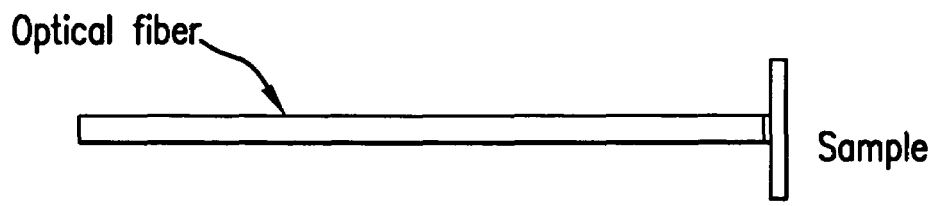
FIG. 10A is a side view of an embodiment according to the invention wherein the optical fiber faces a sample directly.
Figure 10B:
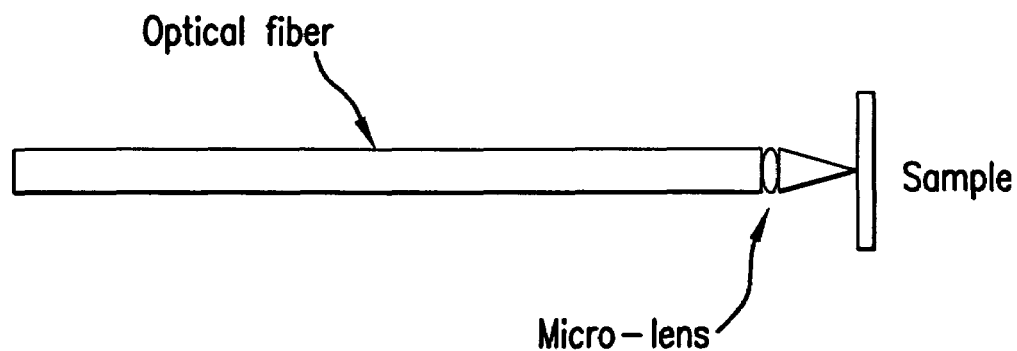
FIG. 10B is a side view of an embodiment according to the invention wherein the laser signal through optical fiber is focused through a micro-lens.
Figure 10C:
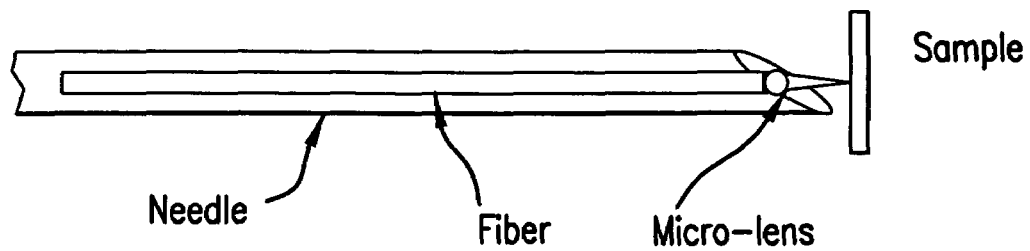
FIG. 10C is a side view of an embodiment according to the invention wherein the optical fiber is directed to the sample through a needle.

FIGS. 10A, 10B and 10C demonstrate, for instance, three different schematics of an LIBS probe for cancer detection:

In FIG. 10A, a fiber carrying an intense laser light is directly pointed at the sample tissue cells. Because of the high intensity of the laser beam, the laser induced breakdown takes place and the corresponding LIBS signal is carried back to the spectrometer. This type of arrangement is known for the analysis of solid material submersed in water or other liquid [7] but it has not been previously demonstrated with a biological sample.

Another schematic, as shown in FIG. 10B, incorporates a fiber having micro-lens on its tip facing the sample surface. Using this type of arrangement it is possible to focus the laser beam precisely on the surface of the tissue sample. Hence, an increased spatial precision can be achieved.

In a third schematic, as shown in FIG. 10C, an optical fiber as in FIG. 10A (not shown), or an optical fiber with a micro-lens as in FIG. 10B (shown), can be inserted in a needle that is used to guide the fiber to the deep lying tissues in a bulk of human tissue cells. For physicians this schematic is well suited so that an optical fiber can be inserted within the fiber-carrying needle to the suspected cancerous area.

Materials and Methods

Haemangiosarcoma, and normal tissue biopsies (1 $cm^3$) were taken from the liver of a dog, placed on a drop of OCT embedding medium (BDH) on a square of Whatman filter paper (5 $cm^2$) and cooled in nitrogen vapor before immersion in liquid nitrogen. Sections (8 µm) were cut using a "Cryocut" cryostat (Reichert-Jung), air died and then fixed in acetone (10 min) and air dried.

Figure 3A:
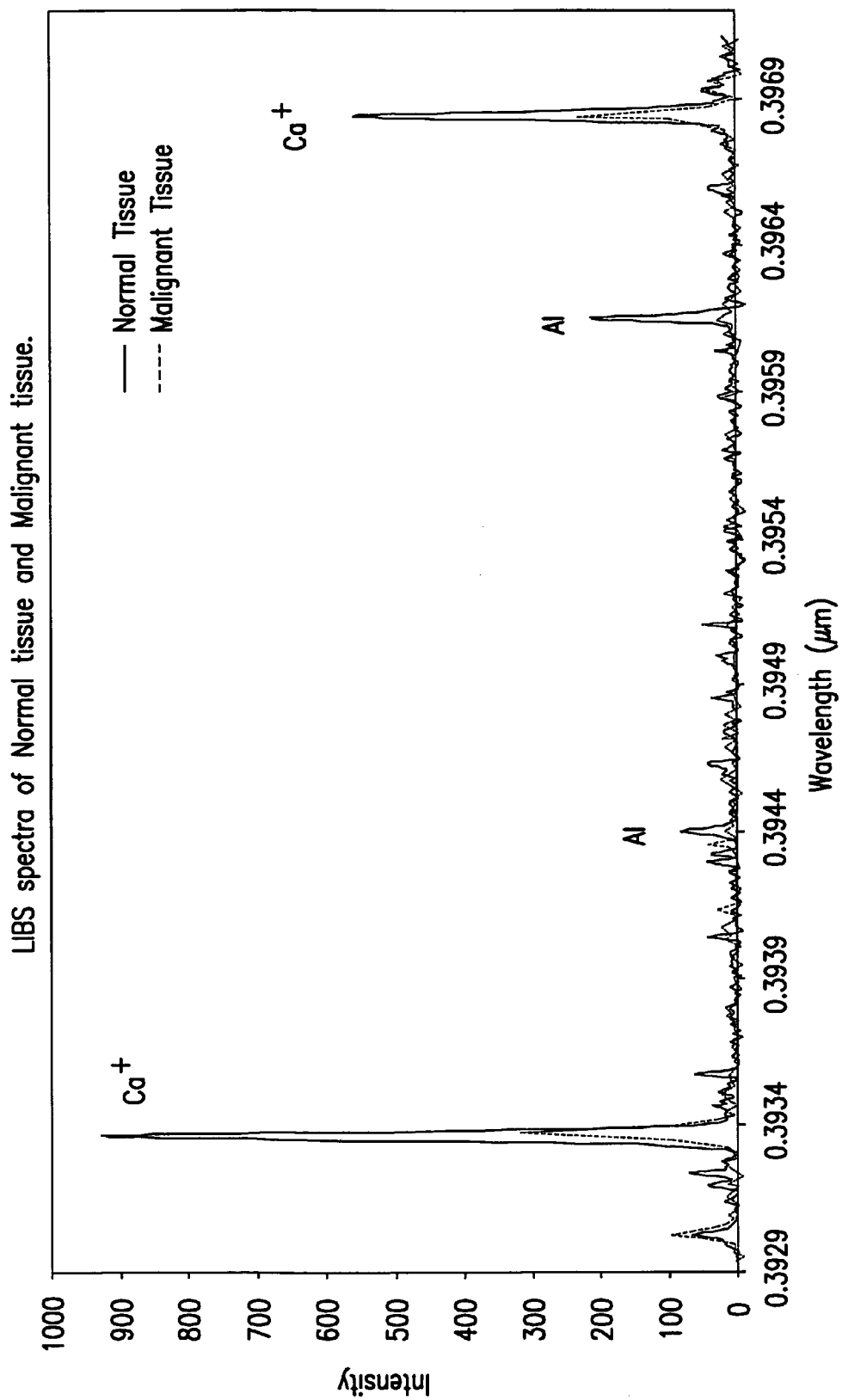
FIG. 3A is a graphical representation of an LIBS spectra of normal tissue juxtaposed with an LIBS spectra of malignant tissue at a wavelength showing Ca and Al intensities for the two samples.
Figure 3B:
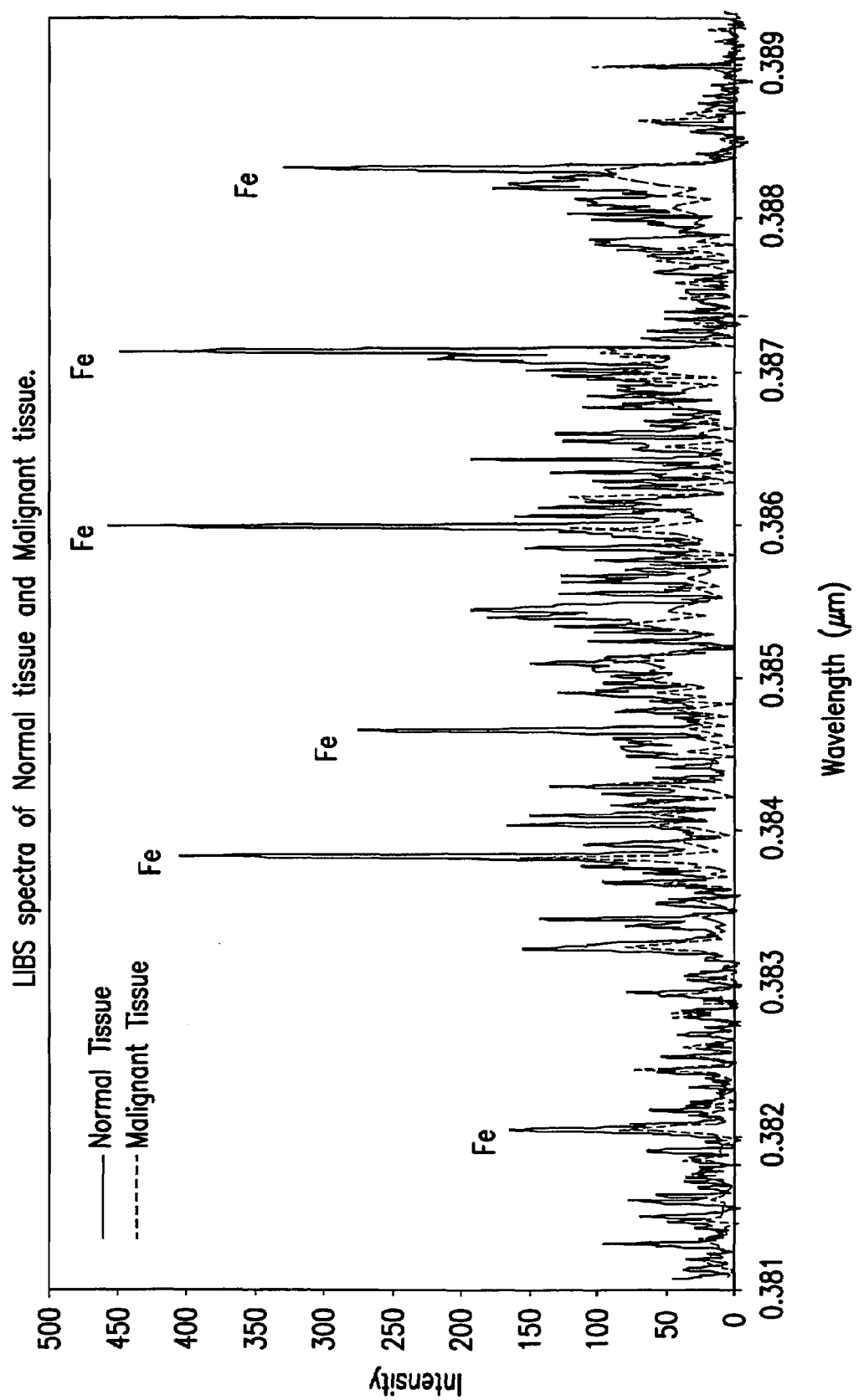
FIG. 3B is a graphical representation of an LIBS spectra of normal tissue juxtaposed with an LIBS spectra of malignant tissue at a wavelength showing Fe intensities for the two samples.

Preliminary experiments on a canine haemangiosarcoma have been completed. FIGS. 3A and 3B align the spectra of normal tissue with the spectra of malignant tissue. It is clear that the line intensities of calcium (FIG. 3A) and iron (FIG. 3B) are lower in the spectrum for neoplastic tissue. Also aluminum (FIG. 3A) is present in the normal tissue but not on the neoplastic tissue.[8]

Figure 4A:
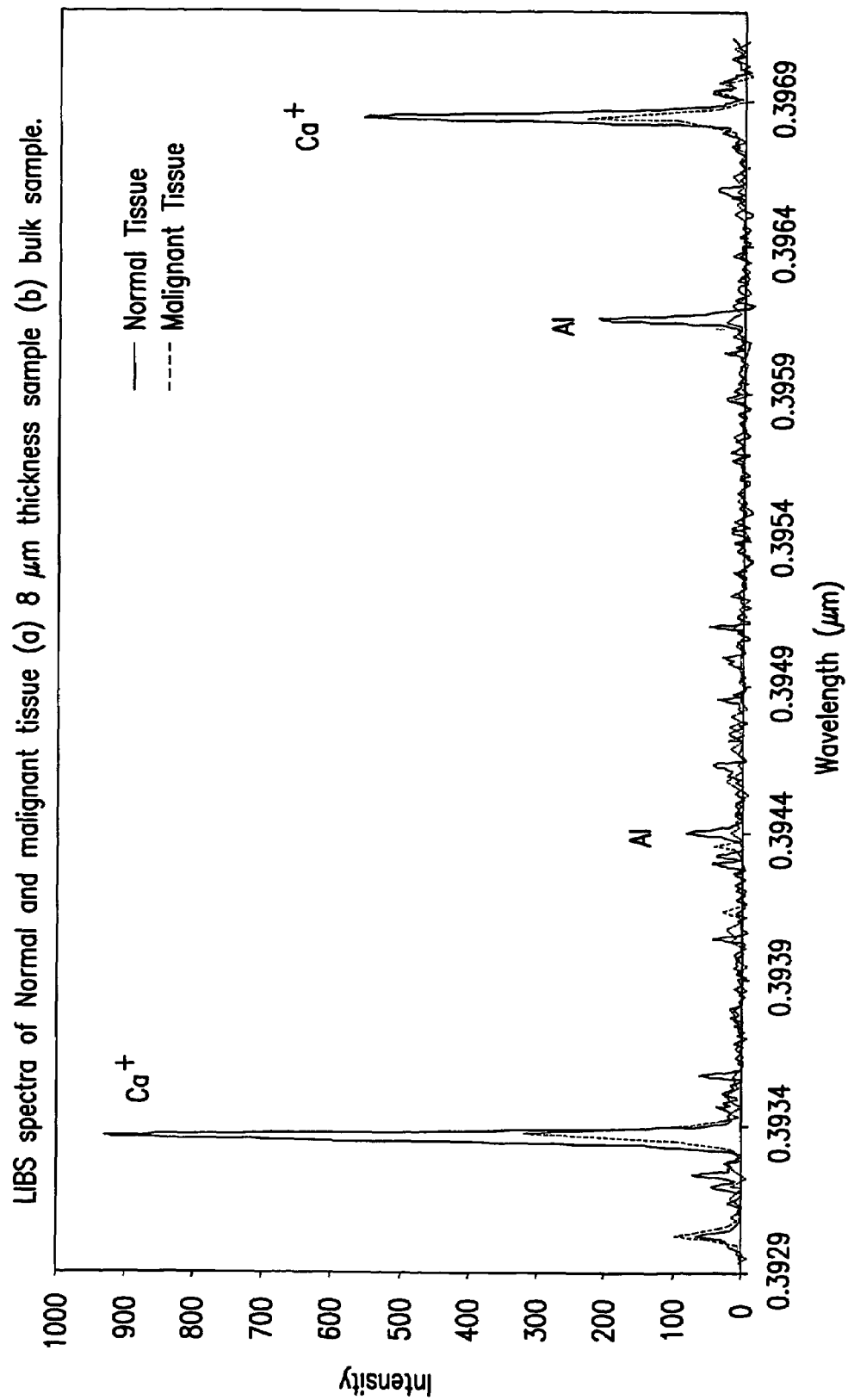
FIG. 4A is a graphical representation of an LIBS spectra of normal tissue juxtaposed with an LIBS spectra of malignant tissue for tissue samples that are 8 µm thin.
Figure 4B:
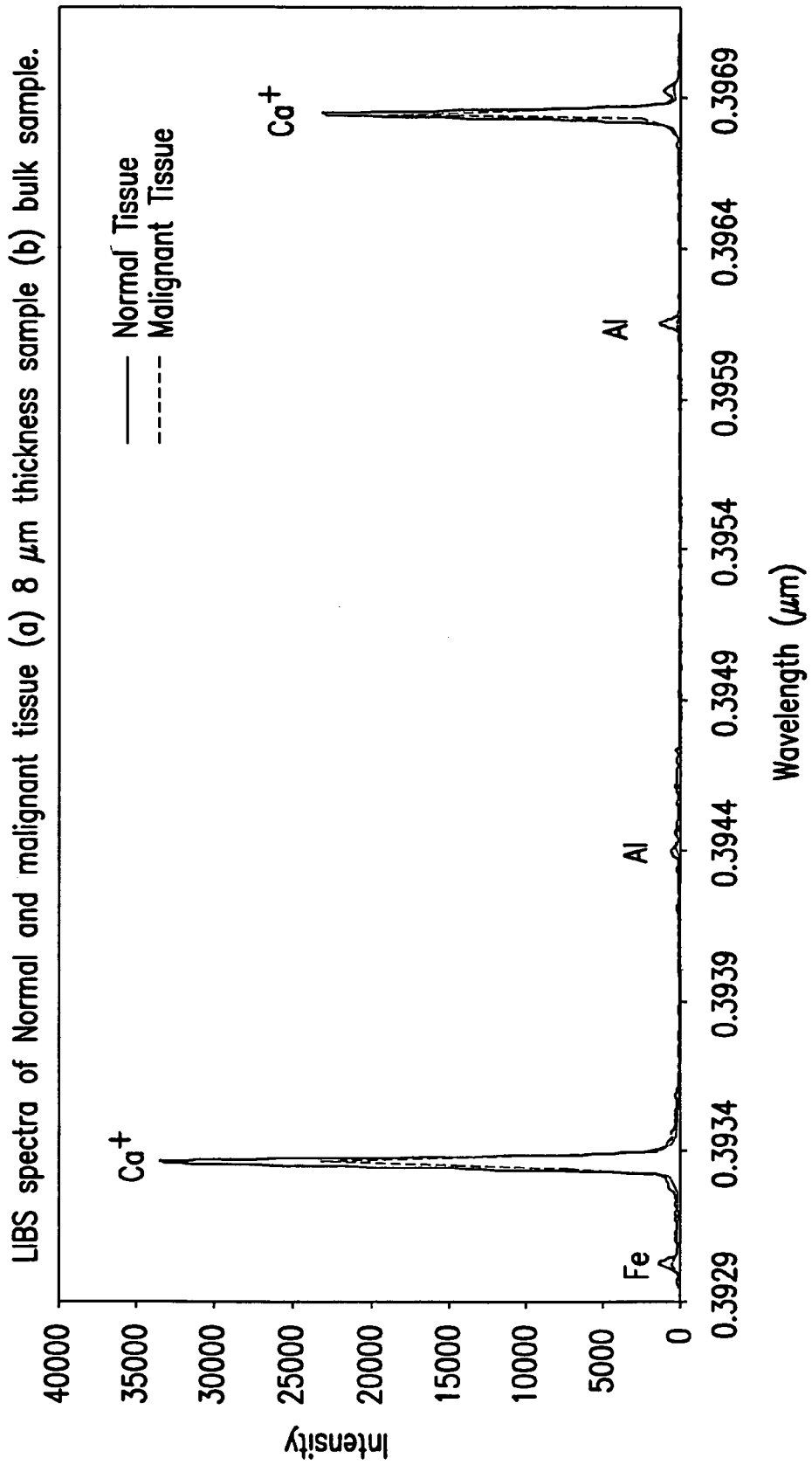
FIG. 4B is a graphical representation of an LIBS spectra of normal tissue juxtaposed with an LIBS spectra of malignant tissue for a tissue sample that is thick, in a bulk sample.

FIGS. 4A and 4B show the LIBS spectra of normal and malignant tissue for relatively thin and thicker bulk samples together. In a bulk sample (FIG. 4B) the spectra intensity is significantly higher than the thinner sample (FIG. 4A). The LIBS technology works satisfactorily both for the thick and thin tissue cells.

Figure 5:
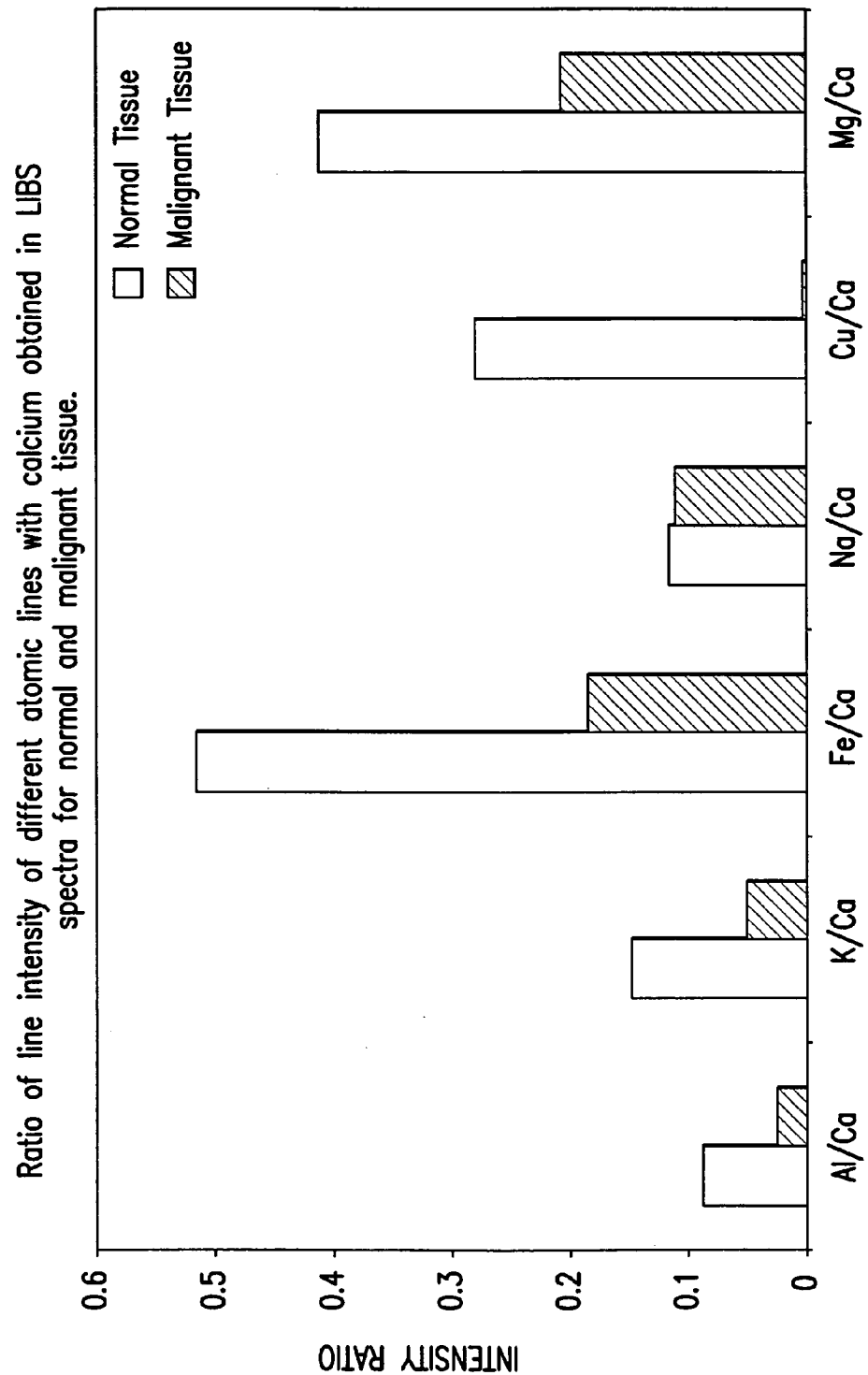
FIG. 5 is a graphical representation showing the ratio of the lines of intensity of different elemental atomic lines with calcium lines obtained from LIBS spectra for both normal and malignant tissue.

The ratio of intensity of atomic lines for different elements with calcium in both malignant and nonmalignant tissue are compared in FIG. 5. It is evident that the ratio is lower for almost all the elements in malignant tissue cells in comparison to normal cells. The ratio is drastically lower in the case of copper. Accordingly, a clear distinction between normal and malignant tissue is observable in FIG. 5. Analytical computer software uses this information of the ratio of line intensity to quickly assimilate data about the tissue, and report whether it is malignant or nonmalignant.

Figure 6:
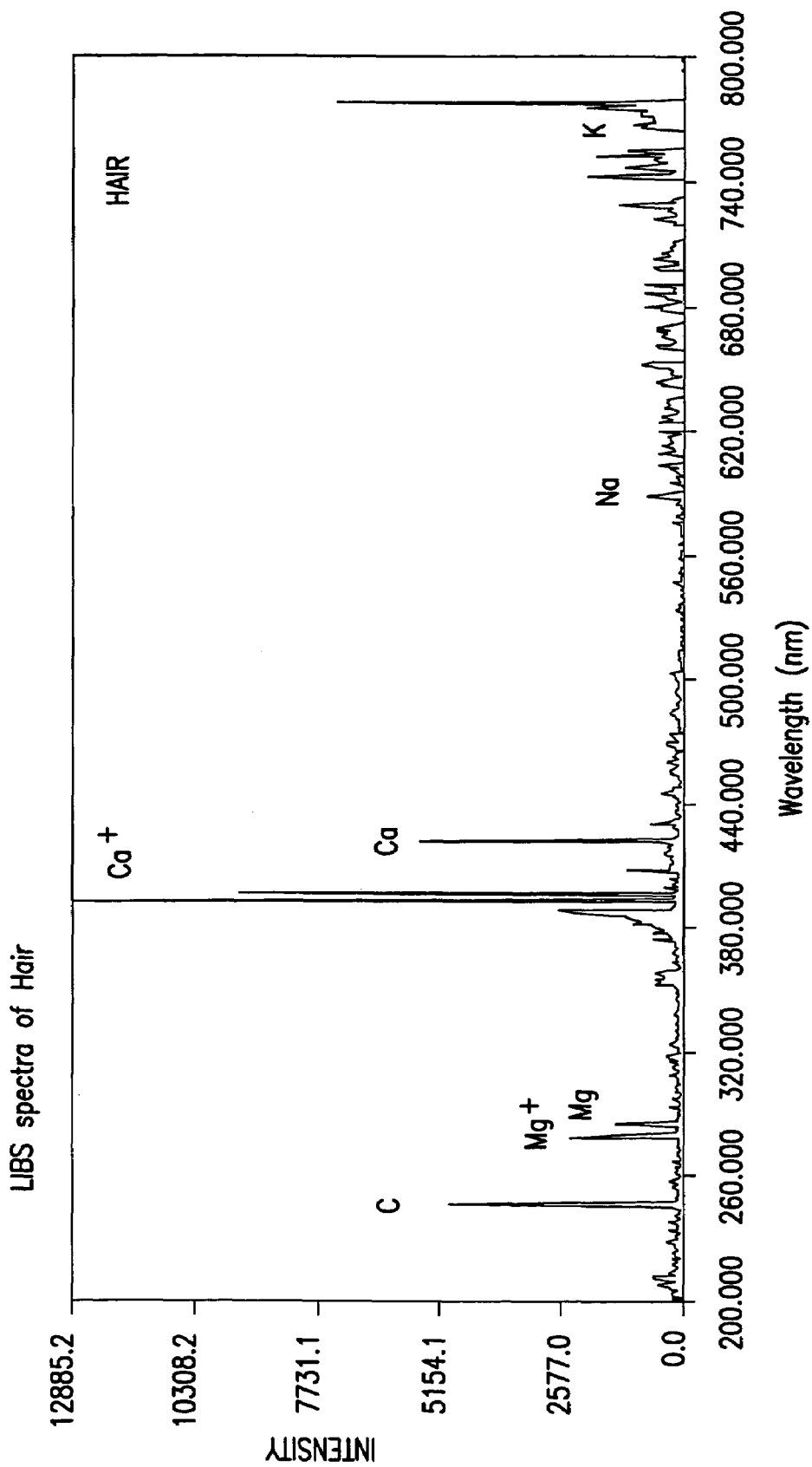
FIG. 6 is a graphical representation showing the LIBS spectrum for a hair sample.
Figure 7:
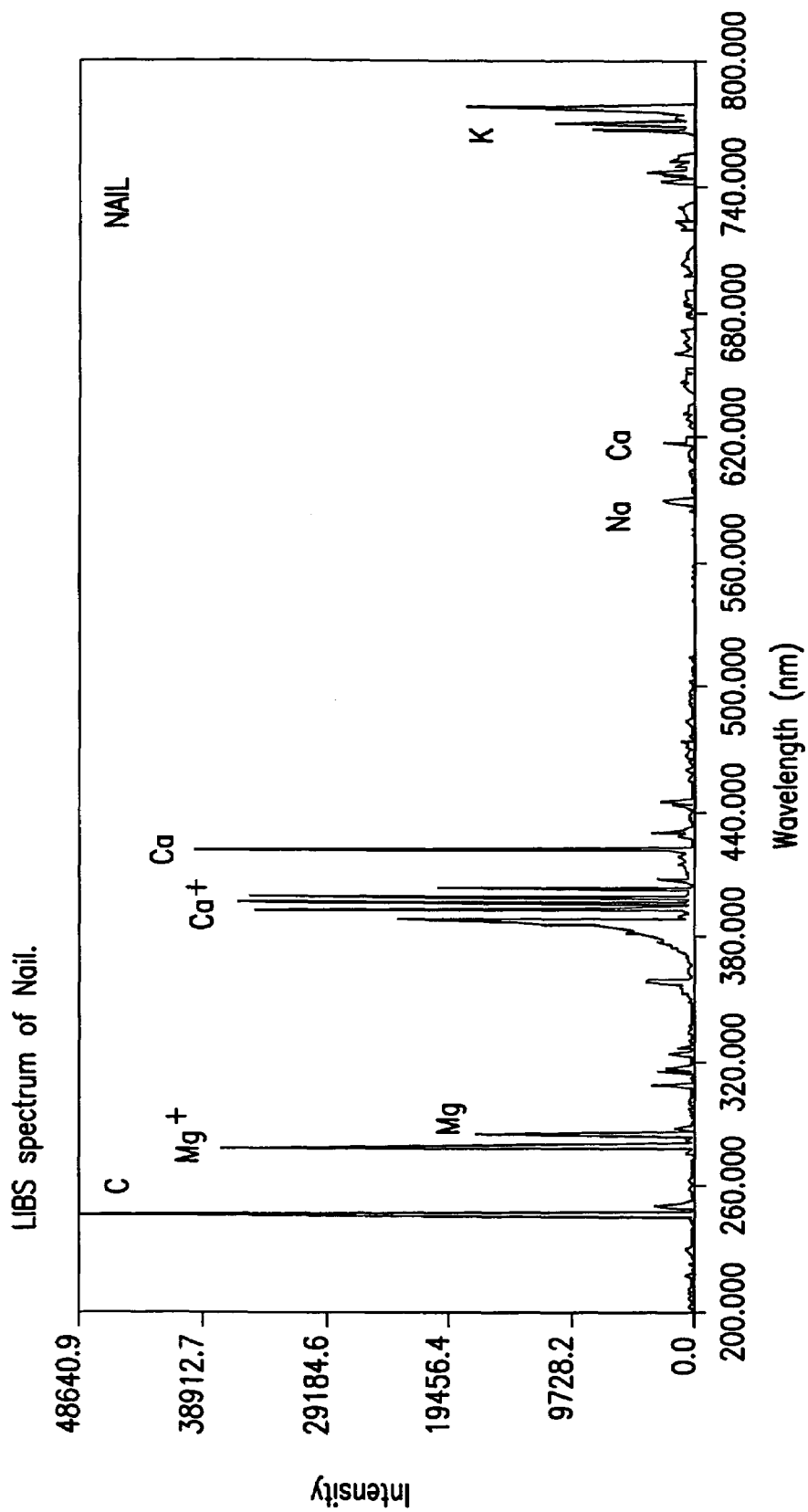
FIG. 7 is a graphical representation showing the LIBS spectrum for a nail sample.
Figure 8A:
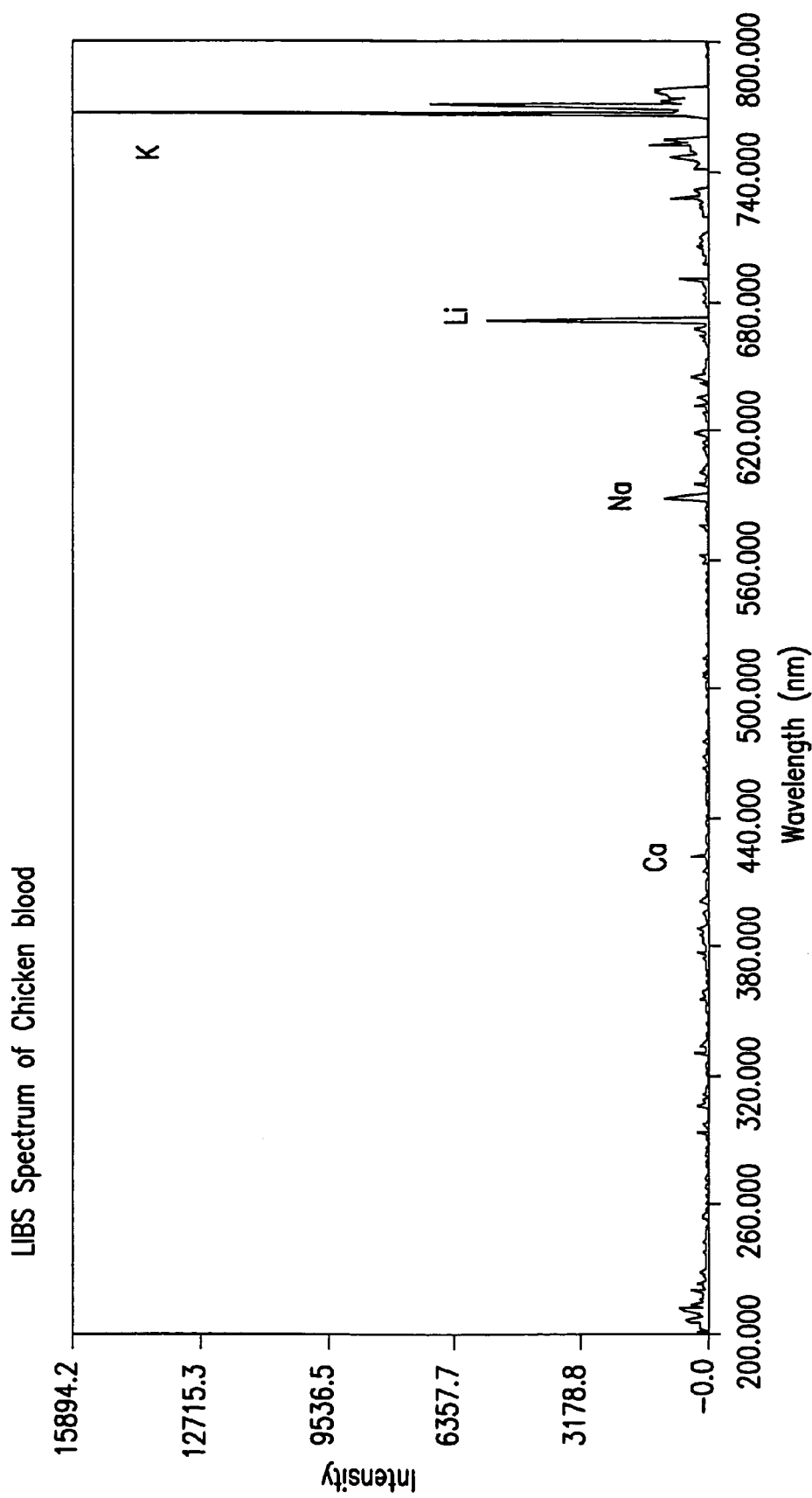
FIG. 8A is a graphical representation showing the LIBS spectrum for chicken blood along a broad spectrum.
Figure 8B:
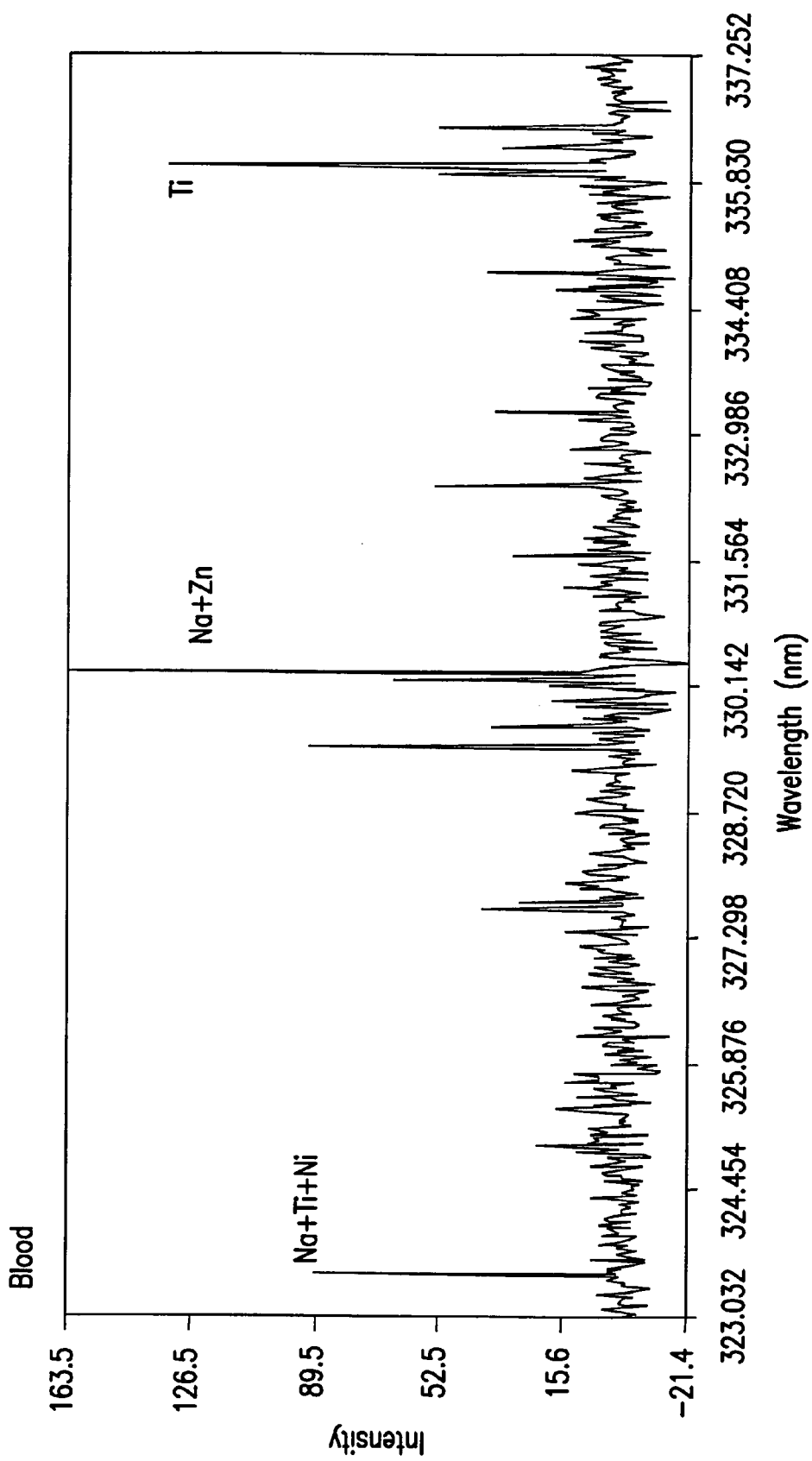
FIG. 8B is a graphical representation showing the LIBS spectrum for chicken blood along a narrow spectrum.

LIBS spectrum is also used, according to the invention, to identify the source of a sample and for other forensic uses. An LIBS spectrum for hair is shown in FIG. 6. The lines for magnesium, calcium, carbon and sodium are very strong, and the lines for sodium and potassium are very weak. An LIBS spectrum for nail is given in FIG. 7. The pattern for FIG. 6 and FIG. 7 are very similar except that the lines for carbon and magnesium are stronger in comparison to calcium lines in nail than to those for hair. The spectra of FIGS. 6 & 7 are recorded under similar experimental conditions at a laser energy of 20 mJ, CCD gate delay of 1µs and gate width of 10µs. From the spectra of hair and nail one can observe the similarity of their structure.[9] Performing the LIBS methodology with a nail sample is less cumbersome in comparison to hair because with the large flat area of the nail there is no need for special alignment of the laser focal point to the nail surface as needed in case of hair. Also the nail is firmer and more solid in comparison with hair and the LIBS result is more pronounced. For the nail, intensity is approximately three times that in comparison to hair. In LIBS literature this phenomena is described as the matrix effect.[3,4] An LIBS spectrum of chicken blood is shown in FIG. 8. In a chicken blood sample, the lines for calcium, sodium, lithium, and potassium are strongly apparent. This can be compared with the lower intensity of other compounds along the spectrum as shown in FIG. 8B and the profile can be drawn for either or both parts of this whole spectrum.

EXAMPLE 1

A device is constructed for detecting the presence and/or concentration of at least one chemical element in a biological or other organic specimen. The device comprises a probe; a laser light source; a detector all directed on the specimen. The specimen may be analyzed in vivo, or separate from the host organism. The specimen may, for instance, be blood, nail, hair, tissue from any part of a human, other animal, plant, or combinations thereof.

EXAMPLE 2

According to this embodiment is an apparatus in which the laser light is transmitted to the probe through a harmonic separator for directing a laser light from the laser light source; a dichroic mirror for reflecting the laser light from the harmonic separator; and a coupling lens for coupling the laser light at an input end of a multi-modal optical fiber. In another embodiment of the invention, the apparatus further comprises a data acquisition-analysis system.

EXAMPLE 3

Another embodiment of the invention is a method for detecting the concentration of at least one chemical element in a specimen. The method comprises directing the laser light onto the specimen; atomizing a portion of the specimen with the laser light; and evaluating the light emitted from the atomized portion to determine the concentration of at least one chemical element.

EXAMPLE 4

In another embodiment of the invention, there is a method for detecting the concentration of at least one chemical element in a specimen. The method comprises placing a probe in close proximity to the specimen; directing a laser light through the probe onto the specimen; atomizing a portion of the specimen with the laser light; and evaluating the light emitted from the atomized portion to determine the concentrations of the chemical element.

EXAMPLE 5

In another embodiment of this invention is a system and method for evaluating the light emitted from the atomized portion of a sample by calculating the concentration of at least one chemical element from a specimen; comparing the concentration of the chemical element in the specimen with the normal range of concentrations of the chemical element in a standard; and classifying the specimen as normal or abnormal. In this system and method the light emitted from the atomized portion of the specimen can, optionally, be evaluated using a data acquisition/analysis system with optionally a separate data processor.

EXAMPLE 6

In another embodiment of this invention, the classification of the specimen as normal or abnormal is used to assess the health of the host from which the specimen is obtained.

It will be recognized by those skilled in the art that changes could be made to the above-described embodiments of the invention without departing from the broad inventive concepts thereof. It is understood, therefore, that this invention is not limited to the particular embodiments disclosed, but is intended to cover all modifications which are within the spirit and scope of the invention and that this invention is not limited to the particular embodiments disclosed, but it is intended to cover any modifications which are within the spirit and scope of the present invention as defined by the appended claims.

REFERENCES

1. Jemal, A., Murray, T., Samuels, A., Ghafoor, A., Ward, E., Thun, M. J. (2003), "Cancer statistics, 2003" CA Cancer J. Clin., Vol. 53, 5–26.

2. Cancer Facts and Figures 2003: American Cancer Society, www.cancer.org.

3. Srinivas, P. R., Srivastava, S., Hanash, S., Wright Jr., G. L., (2001), "Proteomics in Early Detection of Cancer", Clin. Chem., 47:10, 1901–1911.

4. Ramanujam, N., Chen, J. X., Gossage, K., Kortum, R. R. and Chance, B., (2001), "Fast and Noninvasive Fluorescence Imaging of Biological Tissues in vivo using a Flying-Spot Scanner", IEEE Trans. on Biomed. Engg., Vol. 48, No. 9, 1034–1041.

5. Ntziachristos, V., Brenner C., and Weissleder, R., (2003), "Fluorescence imaging with near-infrared light: new technological advances that enable in vivo molecular imaging", Eur. Radiol., Vol 13, 195–208.

6. Yueh, F. Y., Singh, J. P., and Zhang, H. "Elemental Analysis with Laser Induced Breakdown Spectroscopy", In Encyclopedia of Analytical Chemistry, John Wiley and Sons. Ltd, Chisheter, U.K., 2000.

7. Radziemski, L J., and Cremers, D. A. (1989). "Laser Induced Plasma and Applications," Marcel Dekker, New York, NY.

8. Thiem, T. L., Salter, R. H., Gardner, J. A., Lee, Y. I., and Sneddon, J. (1994), Appl. Spectrosc., 48, 58.

9. Rusak, D. A., Castle, B. C., Smith, B W., and Winefordner, J. D. (1997), Crit. Rev. Anal. Chem., 27, 257.

10. Rai, A. K., Yueh, F. Y., and Singh, J. P. (2002), "High Temperature Laser-Induced Breakdown Spectroscopy for analysis of molten Alloy constituents" Rev. Sci. Instrum. 73, 3589–3599.

11. Sarnek, 0., Beddows, D. C. S., Kaiser, J., Kukhlevsky, S. V., Liska, M., Telle, H. H., and Young, J., (2000), Opt. Eng. 38, 2248.

12. Kwaitek, W. M., Drewniak, T., Lekka, M., Wajdowicz, A., (1996) Nuclear Instruments and Methods in Physics Research B 109/100 284–288.

13. Nidal M. Ershaidat and Sami H. Mahmood, See http://conference.ke.ip/JASS02/26 nidal.pdf.

21. Kumar, A., Yueh, F. Y., Singh, J. P., (2003). "Characterization of Malignant Tissue Cells Using laser Induced Breakdown Spectroscopy" Optics Express (under review).

22. Kumar, A., Yueh, F. Y., Singh, J. P., (2003). "Laser Induced Breakdown Spectroscopy: Application to Life Sciences" Mississippi State University, Invention Disclosure No. 03-0414-50.

23. C. W. Ng and N. H. Cheung, "Detection of Sodium and Potassium in Single Human Red Blood Cells by 193 nm Laser Ablative Sampling: A Feasibility Demonstration", Analytical Chemistry 2000, 72, 247–250.

What is claimed is:

1. A laser-induced breakdown spectroscopy (LIBS) apparatus for detecting cancer comprising:
   a laser light source;
   a probe for directing laser light from the laser light source to a sample in vivo to generate an emission spectrum;
   a detector for detecting the emission spectrum; and
   a processor for analyzing the emission spectrum to detect a cancer in the sample.

2. The apparatus according to claim 1, and further comprising a data acquisition or analysis system with optionally a separate data processor.

3. The apparatus according to claim 1, in which the laser light is transmitted to the probe through a harmonic separator for directing laser light from the laser light source.

4. The apparatus according to claim 3, further comprising a diebroic mirror for reflecting the laser light from the harmonic separator.

5. The apparatus according to claim 1, further comprising a coupling lens for coupling the laser light at an input end of a multi-modal optical fiber.

6. The apparatus according to claim 1, wherein the emission spectrum is collected either in the same fiber or in another fiber to travel in a backward direction to a spectrometer.

7. The apparatus according to claim 1, wherein the laser light source is a $CO_2$ laser, a Ruby laser, a long-pulse YAG laser, an Alexandrite laser, an ER:YAG laser, an intense pulsed light laser, a KTP laser, a diode laser, or a pulse dye laser.

8. The apparatus according to claim 1, wherein the laser light source is a pulsed Nd:YAG laser.

9. The apparatus according to claim 1, wherein the apparatus is part of a laser scalpel.

10. The apparatus of claim 1, wherein the cancer is detected by analyzing a content of a trace element in the sample.

11. The apparatus of claim 10, wherein the trace element is a metal.

12. The apparatus of claim 10, wherein the trace element is calcium.

13. The apparatus of claim 10, wherein the trace element is aluminum.

14. The apparatus of claim 10, wherein the trace element is iron.

15. The apparatus of claim 10, wherein the trace element is copper.

16. The apparatus of claim 1, wherein the detector is a spectrograph.

17. The apparatus of claim 1, wherein the cancer is selected from the group consisting of bladder, colon, endometrial, lung, ovarian, prostate and rectal cancer.

18. A method of using a laser-induced breakdown spectroscopy (LIBS) system for detecting cancer, said method comprising:
    directing laser light from a laser light source to a biological sample;
    generating an emission spectrum from the biological sample;
    detecting the emission spectrum; and
    analyzing the emission spectrum to detect cancer.

19. The method according to claim 18, further comprising:
    comparing the emission spectrum with a control emission spectrum to determine whether the biological sample is malignant.

20. The method according to claim 18, further comprising:
    analyzing the emission spectrum to determine the presence or absence of at least one trace element.

21. The method according to claim 18, further comprising:
    analyzing the emission spectrum to determine the quantity of at least one trace element.

22. The method according to claim 18, further comprising:
    evaluating the light emitted from the sample by calculating the concentration of at least one chemical element from a sample;
    comparing the concentration of the chemical element in the sample with a range of concentrations of the chemical element in a standard; and
    classifying the sample as normal or abnormal.

23. The method according to claim 18, further comprising:
    directing the laser light through a probe onto the sample in vivo.

24. The method according to claim 18, wherein the sample is selected from the group consisting of: blood, nail, hair, tissue or biological fluid.

25. The method according to claim 18, wherein the method is practiced to detect breast cancer.

26. The method according to claim 18, wherein the method is practiced utilizing a laser scalpel.

27. The method of claim 26, wherein the biological sample is a neoplastic mass, and the emission spectrum is analyzed in real time, whereby the neoplastic mass can be removed using the laser scalpel while sparing a maximum amount of healthy tissue.

28. The method of claim 18, wherein the cancer is selected from the group consisting of bladder, colon, endometrial, lung, ovarian, prostate and rectal cancer.

29. The method of claim 21, wherein the at least one trace element is a metal.

30. The method of claim 29, wherein the at least one trace element is calcium.

31. The method of claim 29, wherein the at least one trace element is aluminum.

32. The method of claim 29, wherein the at least one trace element is iron.

33. The method of claim 29, wherein the at least one trace element is copper.

* * * * *

UNITED STATES PATENT AND TRADEMARK OFFICE
CERTIFICATE OF CORRECTION

PATENT NO.         : 7,092,087 B2
APPLICATION NO. : 10/662347
DATED                  : August 15, 2006
INVENTOR(S)       : Akshaya Kumar et al.

It is certified that error appears in the above-identified patent and that said Letters Patent is hereby corrected as shown below:

Column 2, line 59, USPTO error:

"spectroscopy (LIZBS)" to --spectroscopy (LIBS)--

Column 4, line 25, Applicant error:

"nant tissue at a wavelength showing Ca and Al intensities for" to --nant tissue at a wavelength region showing Ca and Al intensities for--

Column 4, line 29, Applicant error:

"nant tissue at a wavelength showing Fe intensities for the" to --nant tissue at a wavelength region showing Fe intensities for the--

Figure 9A:
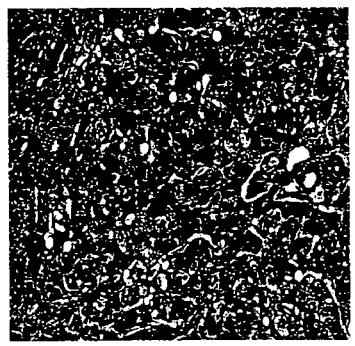
FIG. 9A is a photograph of liver cells taken from the biopsy of a dog liver and showing normal liver cells.
Figure 9B:
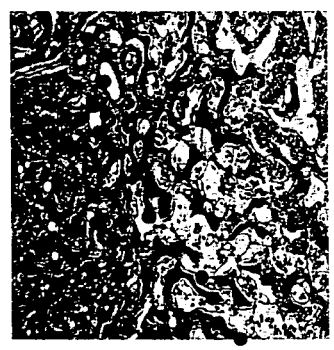
FIG. 9B is a photograph of liver cells taken from the biopsy of a dog liver showing full hemangiosarcoma.
Figure 9C:

Column 4, line 53, USPTO error:

"FIG. 9C is a photograph of liver cells taken from the biopsy of a dog liver showing full hemangiosarcoma with haemoragic area arrowed;" is missing Column 5, line 24, Applicant error:

"such blood, tissue, nail or hair.[…]" to --such as blood, tissue, nail or hair.[…]--

Column 8, line 45, Applicant error:

"a laser energy of 20 mJ, CCD […]" to --a laser energy of 20 mJ, ICCD […]--

Column 10, lines 45-55, USPTO error:

Please delete lines 45-55

UNITED STATES PATENT AND TRADEMARK OFFICE
CERTIFICATE OF CORRECTION

PATENT NO. : 7,092,087 B2
APPLICATION NO. : 10/662347
DATED : August 15, 2006
INVENTOR(S) : Akshaya Kumar et al.

It is certified that error appears in the above-identified patent and that said Letters Patent is hereby corrected as shown below:

Column 11, line 5, USPTO error:

"a diebroic [...]" to --a dichroic [...]--

Signed and Sealed this

Sixth Day of February, 2007

JON W. DUDAS
*Director of the United States Patent and Trademark Office*